US005527666A

United States Patent [19]
De Rossi et al.

[11] Patent Number: 5,527,666
[45] Date of Patent: Jun. 18, 1996

[54] METHOD FOR THE DIAGNOSIS IN VITRO OF HIV-1 VIRUS INFECTIONS

[75] Inventors: Anita De Rossi, Padua; Marcella Pasti, Verona; Fabrizio Mammano, Padua; Marina Panozzo, Canove; Monica Dettin, Padua; Carlo Di Bello, Padua; Luigi Chieco-Bianchi, Padua, all of Italy

[73] Assignees: Istituto Superiore Di Sanita'; Consiglio Nazionale Delle Ricerche, both of Rome, Italy

[21] Appl. No.: 97,751

[22] Filed: Jul. 23, 1993

[60] Related Application Data

Continuation in part of PCT/EP92/00187, Jan. 19, 1992. Published as WD92/13882, Aug. 20, 1992.

[30] Foreign Application Priority Data

Jan. 30, 1991 [IT] Italy .................................. MI92A0220

[51] Int. Cl.$^6$ ........................................................ C12Q 1/70

[52] U.S. Cl. ......................... 435/5; 435/240.1; 435/240.2; 435/240.23; 435/974; 530/325; 530/326

[58] Field of Search .......................... 435/7.1, 5, 7.9–.95, 435/974, 240.1, 240.2, 240.23; 530/324–326

[56] References Cited

U.S. PATENT DOCUMENTS 5,017,688 5/1991 Gilbert et al. .......................... 530/326

FOREIGN PATENT DOCUMENTS 9003984 4/1990 WIPO .
9015078 12/1990 WIPO .

OTHER PUBLICATIONS

Matsushita et al, "Characterization of a HIV Neutralizing Monoclonal Antibody & Mapping of the Neutralizing Epitope" *J. Virol* vol. 62, No. 6 pp. 2107–2114 (1988).

Devash et al, "C–Terminal Fragments of gp120 & Synthetic Peptides from 5 HTLV–III Strains: Prevalence of Antibodies to the HTLV–III–MN Isotate in Infected Individuals." *AIDS Res & Hum Retrov* vol. 6, No. 3 pp. 307–316 (1990).

Autiero et al., Journal of Virology, 185, pp. 820–828 (1991).

Rusche et al., Proc. Nat'l. Acad. Sci., vol. 85, pp. 3198–3202 (1988).

*Primary Examiner*—Christine M. Nucker
*Assistant Examiner*—Jeffrey Stucker
*Attorney, Agent, or Firm*—Hedman, Gibson & Costigan

[57] ABSTRACT

A method for the diagnosis in vitro of HIV-1 infections by treating CD4-positive cells infected with blood and other biological materials with synthetic peptides derived from V3 region of HTLV-III B strain and from MN strain of HIV-1 virus is reported. The above peptides enhance the infectivity of HIV-1 virus in cellular cultures in vitro.

3 Claims, 13 Drawing Sheets

CONVERSION %  >99  >99 >99  90.0 51.5 37.8 34.1 39.2 34.6

PEPTIDE CONCENTRATION (μM)

DB3

CONVERSION % >99 >99  91.2  80.2 47.2 34.2 31.0 25.3 21.3

PEPTIDE CONCENTRATION (μM)

FIG. 5a (III)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 24 amino acids
( B ) TYPE: amino acid
( C ) TOPOLOGY: circular ( i i ) SEQUENCE DESCRIPTION: SEQ ID NO:1:

```
Asn Asn Thr Arg Lys Ser Ile Arg Ile Gln Arg Gly Pro Gly Arg
 1              5                   10                  15

Ala Phe Val Thr Ile Gly Lys Ile Gly
                20
```

( 2 ) INFORMATION FOR SEQ ID NO:2:

( i ) SEQUENCE CHARACTERISTICS:
( A ) LENGTH: 23 amino acids
( B ) TYPE: amino acid
( C ) TOPOLOGY: circular ( i i ) SEQUENCE DESCRIPTION: SEQ ID NO:2:

Tyr Asn Lys Arg Lys Arg Ile His Ile Gly Pro Gly Arg Ala Phe
1               5                   10                  15
Tyr Thr Thr Lys Asn Ile Ile Gly
                20

METHOD FOR THE DIAGNOSIS IN VITRO OF HIV-1 VIRUS INFECTIONS

This application is a continuation in part of PCT application No. EP92/00187 filed Jan. 29, 1992.

PRIOR ART

A great deal of information is known regarding the characteristics of HIV-1 virus and the peptides derived from V3 region of gp 120.

A characteristic feature of HIV-1 is its genetic variability, and naturally occurring vital variants show distinct biological properties which correlate with the severity of HIV-1 infection in vivo (Asjo, B., L. Morfeldt-Manson, J. Albert, G. Biberfield, A. Karlsson, K. Lidman, and E. M. Fenyo. 1986. Replicative capacity of human immunodeficiency virus from patients with varying severity of HIV infection. Lancet ii: 660–662; Fenyo, E. M., L. Morfeldt-Manson, F. Chiodi, B. Lind, A. Von Gegerfelt, J. Albert, E. Olausson, and B. Asjo. 1988. Distinct replicative and cytopathic characteristics of human immunodeficiency virus isolates. J. Virol. 62: 4414–4419; Fiore, J. R., M. L. Calabrò, G. Angarano, A. De Rossi, G. Fico, G. Pastore, and L. Chieco-Bianchi. 1990. HIV-1 variability and progression to AIDS: a longitudinal study. J. Med. Virol. In press).

Aminoacid sequence mutations on the vital envelope protein (gp 120) may play a critical role in virus infectivity and antigenicity, since the envelope protein mediates virus attachment and penetration on the host cell and induces both humoral and cellular host immune responses (Cordonnier, A., L. Montagnier, and M. Emmerman. 1989. Single amino acid changes in the HIV envelope affect viral tropism and receptor binding. Nature 340: 571–574; Mills, K. H. G., D. F. Nixon, and Andrew J. McMichael. 1989. T-cell strategies in AIDS vaccines: MHC-restricted T-cell responses to HIV proteins. AIDS 3: s101–s110). The principal neutralizing domain (PND) of HIV-1 corresponds to a 24-aminoacid sequence arranged in a loop determined by a disulfide bridge in the third hypervariable region, V3, of the protein gp 120 (Goudsmit, J., C. Debouck, R. H. Meloen, L. Smit, M. Baker, D. M. Asher, A. V. Wolff, C. J. Gibbs, and D. C. Gajdusek. 1988. Human immunodeficiency virus type 1 neutralization epitope with conserved architecture elicits early type-specific antibodies in experimentally infected chimpanzees. Proc. Natl. Acad.).

The antigenic properties of synthetic PND-derived peptides have been inventigated.

Some peptides from the PND of five HTLV-III strains give positive responses when the sera of HTLV-III infected subjects is assayed with the ELISA test (Aids Research and Human Retroviruses, vol. 6, n. 3, 1990, N.Y. pages 307–316, Devash Y. et al.)

Gp 120 fragments from HIV isolates as well as synthetic peptides are bound by a human immunodeficiency virus neutralizing monoclonal antibody (Journal of Virology, Vol. 62, n. 6, 1988, pages 2107, 2114, Matsushita S. et al.).

PND-derived peptides elicit antibodies that in vitro neutralize the infection and prevent fusion of virus-infected cells with uninfected CD4-bearing cells (Rusche, J. R., K. Jvaherian, C. Mc Danal, J. Petro, D. L. Lynn, R. Grimaila, A. Langlois, R. Gallo, L. O. Arthur, J. P. Fischinger, D. P. Bolognesi, S. D. Putney, and T. J. Matthews. 1988. Antibodies that inhibit fusion of human immunodeficiency virus-infected cells bind a 24-amino acid of the vital envelope gp 120. Proc. Natl. Acad. Sci. USA 85: 3198–3202). Moreover, PND-derived peptides evoke virus neutralizing responses in mammals, and they may represent good candidates for vaccine development against AIDS (Goudsmit, J., C. Debouck, R. H. Meloen, L. Smit, M. Bakker, D. M. Asher, A. V. Wolff, C. J. Gibbs, and D. C. Gajdusek. 1988. Human immunodeficiency virus type 1 neutralization epitope with conserved architecture elicits early type-specific antibodies in experimentally infected chimpanzees. Proc. Natl. Acad. Sci. USA 85: 4478–4482; Javaherian, K., A. J. Langlois, C. Mc Danal, K. L. Ross, L. I. Eckler, C. L. Jellis, A. T. Matthews. 1989. Principal neutralizing domain of the human immunodeficiency virus type 1 envelope protein. Proc. Natl. Acad. Sci. USA 86: 6768–6772; La Rosa G. J., J. P. Davide, K. Weinhold, J. A. Waterbury, A. T. Profy, J. A. Lewis, A. J. Langlois, G. R. Dreesman, R. N. Boswell, P. Shadduck, L. H. Holley, M. Karplus, D. P. Bolognesi, T. J. Matthews, E. A. Emini, S. D. Putney. 1990. Conserved sequence and structural elements in the HIV-1 principal neutralizing determinant. Science 249: 932–935).

The central portion of the V3-PND contains a sequence which is highly conserved in different HIV-1 isolated strains, whereas the aminoacids flanking this sequence are variable, and the antibodies elicited by peptides designed from PND of different HIV-1 strains are vital-variant specific, and generally neutralize only the homologous virus.

Nevertheless, in spite of all this knowledge, the biological properties of PND-derived peptides are still unknown and furthermore a still open problem is represented by the insufficient sensitivity of the methods known up to now for the determination of the virus in blood or in others biological materials in subjects whose infection is uncertain.

SUMMARY

The present invention concerns a method for the diagnosis in vitro of HIV-1 infections by treating CD4-positive cells infected with blood and other biological materials with synthetic peptides derived from V3 region of HTLV-III B strain and from MN strain of HIV-1 virus.

This enhancing effect occurs in the early steps of the vital infection and is not virus restricted.

Said peptides have the following aminoacid sequences:

| | |
|---|---|
| NNTRKSIRIQRGPGRAFVTIGKIG | (DB1) |
| YNKRKRIHIGPGRAFYTTKNIIG | (DB3) |

The addition of said peptides to CD4-positive cells cultures enhances the sensitivity of the determination of the virus in blood and in the other biological materials of subjects affected by HIV-1 infection.

Therefore the method of the invention is particularly advantageous because the use of said peptides in cultures in vitro enhance the HIV-1 infection in the uncertain cases in which the infection is limited and the current methods are not sufficiently sensitive.

DETAILED DESCRIPTION OF THE INVENTION

The characteristics and the advantages of the method according to the present invention will be described in the following detailed description.

Said peptides are derived from V3 region of HTLV-III B strain and from MN strain of virus HIV-1 and have the following aminoacid sequences:

NNTRKSIRIQRGPGRAFVTIGKIG            (DB1)

YNKRKRIHIGPGRAFYTTKNIIG             (DB3)

Peptides Synthesis

Synthetic peptides DB1, DB2, DB3 were prepared according to aminoacid sequences of the V3-PND of HIV-1 strains, HTLV-III B, RF and MN respectively.

A modified peptide consisting of 23 aminoacids (DB5) and a DB1 derivative formed by 10 aminoacids (DB6) were also prepared. Said peptides are reported in the following table 1.

TABLE 1

| Peptide | HIV-1 strain | Sequence |
|---------|--------------|----------|
| DB1 | HTLV-III B | N N T R K S I R I Q R G P G R A F V T I G K I G |
| DB2 | RF         | — — — — — — — — T K — — — — V I Y A T — Q I — — |
| DB3 | MN         | Y — K — — R — H — — — — — — — — Y — T K N I — — |
| DB5 | —          | — — V — R — L S — — — — — — — — R — R — — I — — |
| DB6 | —          | — — — — — — — — — — — |

The abbreviations used for the aminoacid are those recommended by IUPAC-IUB Commission on Biochemical Nomenclature (cfr. J. Mol. Biol. 52, 1–17 (1970) and J. Biol. Chem. 247, 977–983 (1972)). The hatchings represent aminoacids identical to those of DB1.

Said peptides may have the terminal or side-chain aminic and/or the carboxylic functions free, salified or protected with suitable alkyl, aryl, alkylaryl and arylalkyl groups.

In particular the carboxylic function in terminal position may be represented by free carboxylic groups or salified with numerous bases, by primary or various by substituted amidic functions, or also by different estereal groups.

The synthesis of the peptide chains was realized by using an automated synthetizer "Applied Biosystems 431 A" starting with 0.5 mmol of a resin previously functionalized with ter-butyloxycarbonyl derivative of the aminoacid of the sequence ending with a carboxylic function.

Hereinbelow, for example, the operating conditions of a peptide synthesis are reported.

The following side-chain protection was used: acetamidoethyl for cystein, benzyl for serin and threonin; p-chlorocarbobenzoxy for lysine, benzylester for aspartic and glutamic acid; tosyl for arginine; 2,4 dinitrophenyl for histidine and 2-bromobenzyloxycarbonyl for tyrosine.

Removal of BOC group was accomplished by a 3 minutes wash with an aqueous solution containing 25% of trifluoroacetic acid, followed by a 16 minutes treatment with 50% trifluoroacetic acid in $CH_2Cl_2$.

BOC protected aminoacids were activated by using dicyclohexylcarbodiimide and introduced as hydroxybenzotriazoles esters.

Each residue incorporation was followed by using an acylation of the free aminic groups by acetic anhydride.

At the end of the synthesis the peptide bonded to the resin was treated with suitable side chain protecting groups and with 10 ml of HF. The reaction mixture was stirred for 1 hour at a temperature ranging from −5° to 0° C.; HF was then removed by Nitrogen flow, and the residue dried under vacuum, was extracted with ethylether and with 30 ml of 30% acetic acid. After lyophylization the peptides were purified by ion exchange chromatography using a Protein Pak SP5PW®, 0.8×7.5 cm Waters column with different gradients of solution B ($Na_2HPO_4$ 10 mM pH6/NaCl 0.5 mM/10%$CH_3CN$) mixed with a solution A ($Na_2HPO_4$ 10 mM, pH6) at a flow rate of 1 ml/min.

Each peptide was then further purified by HPLC on a Delta Pak® column 15μ, 300 Å, 7.8×30 cm using $H_2O$ 0.1% trifluoroacetic acid with a $CH_3CN$ gradient containing 0.1% trifluoroacetic acid.

Each peptide purity was then confirmed by analytical chromatography on Delta Pak 5μ, 100 Å, 3.9×15 cm and resulted higher than 90%. The aminoacid composition was determined with an automated analyzer (Carlo Erba 280).

Vital Infection Tests

MOLT-3 and H938 cells were employed for HIV-1 experiments.

Both these cellular lines have a T-lymphocyte origin and express CD4 molecule.

Cells were maintained in RPMI 1640 medium (Flow Laboratories, Irvine UK) supplemented with 10% fetal calf serum, 2% L-glutamine, and 50 μg/ml gentamycine, and cultured under standard conditions at 37° C. in humidified air containing 5% $CO_2$.

HTLV-III B, RF and MN HIV strain were grown in H9 cells, and the supernatant was collected, centrifugated at 2,000×g for 15 minutes, to remove the cells, and filtered through a 0.22 μm filter.

The virus content was determined by reverse transcriptase (RT) assay and the supernatants were stored at −80° C.

MOLT-3 cells resuspended at a concentration af $2.5 \times 10^6$ cells/ml were plated at 200 μl/well in a 24 wells plate (Costar, Cambridge, Mass., USA) and incubated with 100 μl of a medium containing scalar doses of equimolar amounts of peptides.

After 1 hour, cells were infected with 50 μl of an HIV-1 preparation containing $1 \times 10^5$ cpm/ml of RT activity (0.01 cpm of RT activity cell).

After 1 hour incubation with gentle shaking at 37° C., 1 ml of complete medium was added.

The cells were checked daily at the light microscope for syncytium formation.

After 4 days, supernatants were collected for testing RT assay. H938 cells were plated, treated with peptides and infected as above described and 48 hours after HIV-1 infection, cellular extracts were prepared by 3 cycles of freeze-thawing and tested with CAT (chloramphenicol acetyl transferase) (Gorman, C. M., L. F. Moffat, and B. H. Howard. 1982. Recombinant genomes which express chloramphenicol acetyl transferase in mammalian cells. Mol. Cell. Biol. 2: 1044–1051).

In the cultures treated with MN-derived peptide DB3 and infected with strain HTLV-III B of HV-1, large syncytia were observed within 48 hours from infection (A and B of 
FIG. 1 respectively after 2 and 4 days from infection) while untreated cells showed small syncytia only at 4 days post infection (C of FIG. 1) (D and E represent control trials).

DB3 effect resulted dose dependent, and concentrations as low as 2.5 μM increased syncytium formation within 2 days after HIV-1 infection.

Cultures treated with peptides DB1, derived from HTLV-III B strain, showed an increase in syncytium formation only at peptides doses of 10 and 20 μM.

No such effect occurred in cultures treated with DB2, DB5 and DB6.

Figure 1:
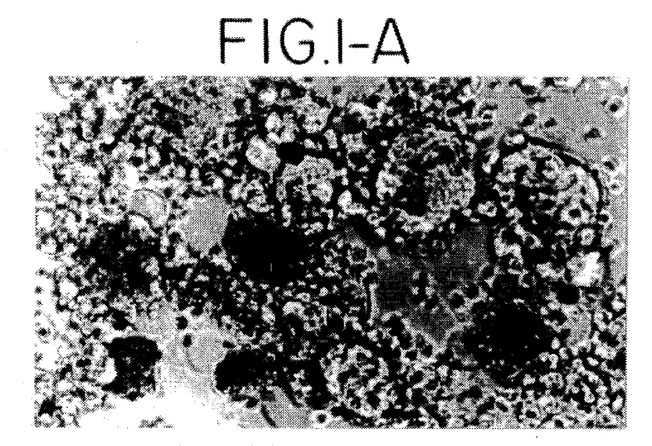
Figure 2:
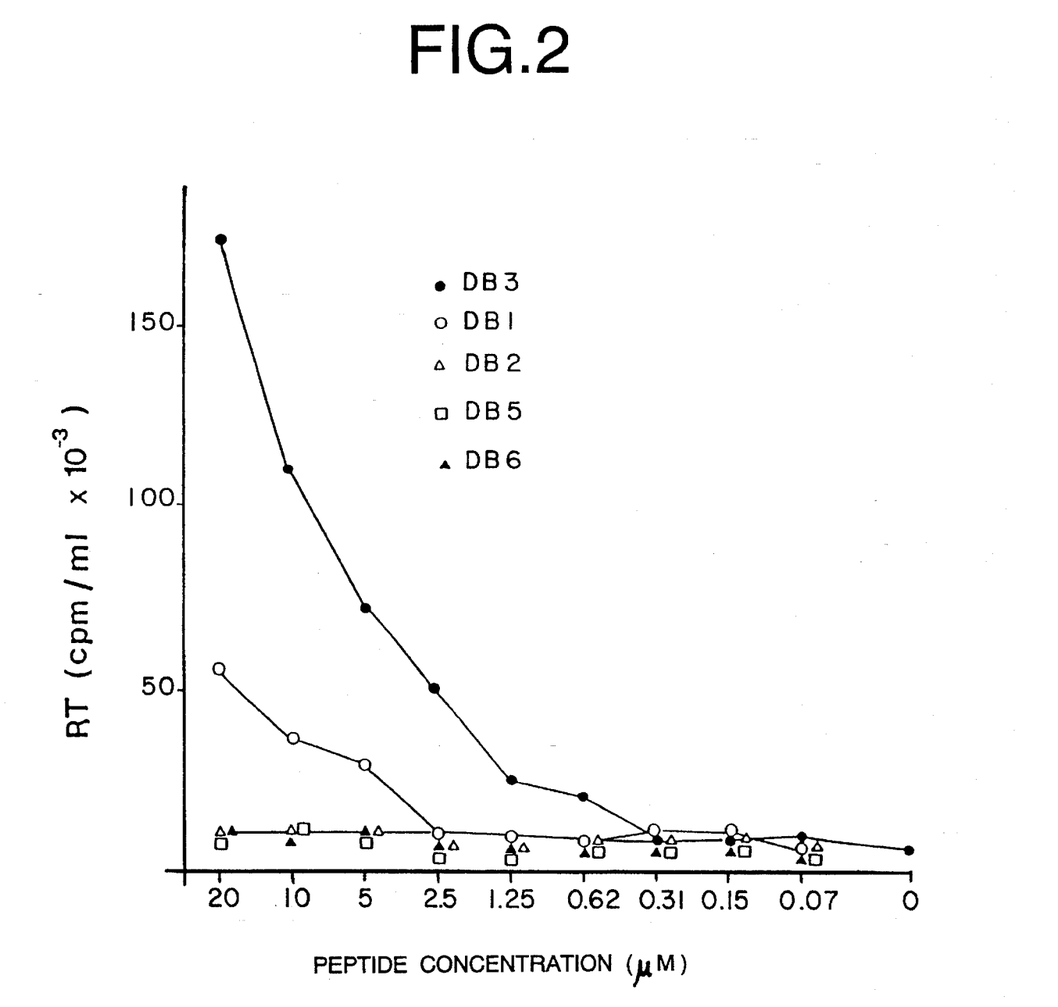
Figure 3:
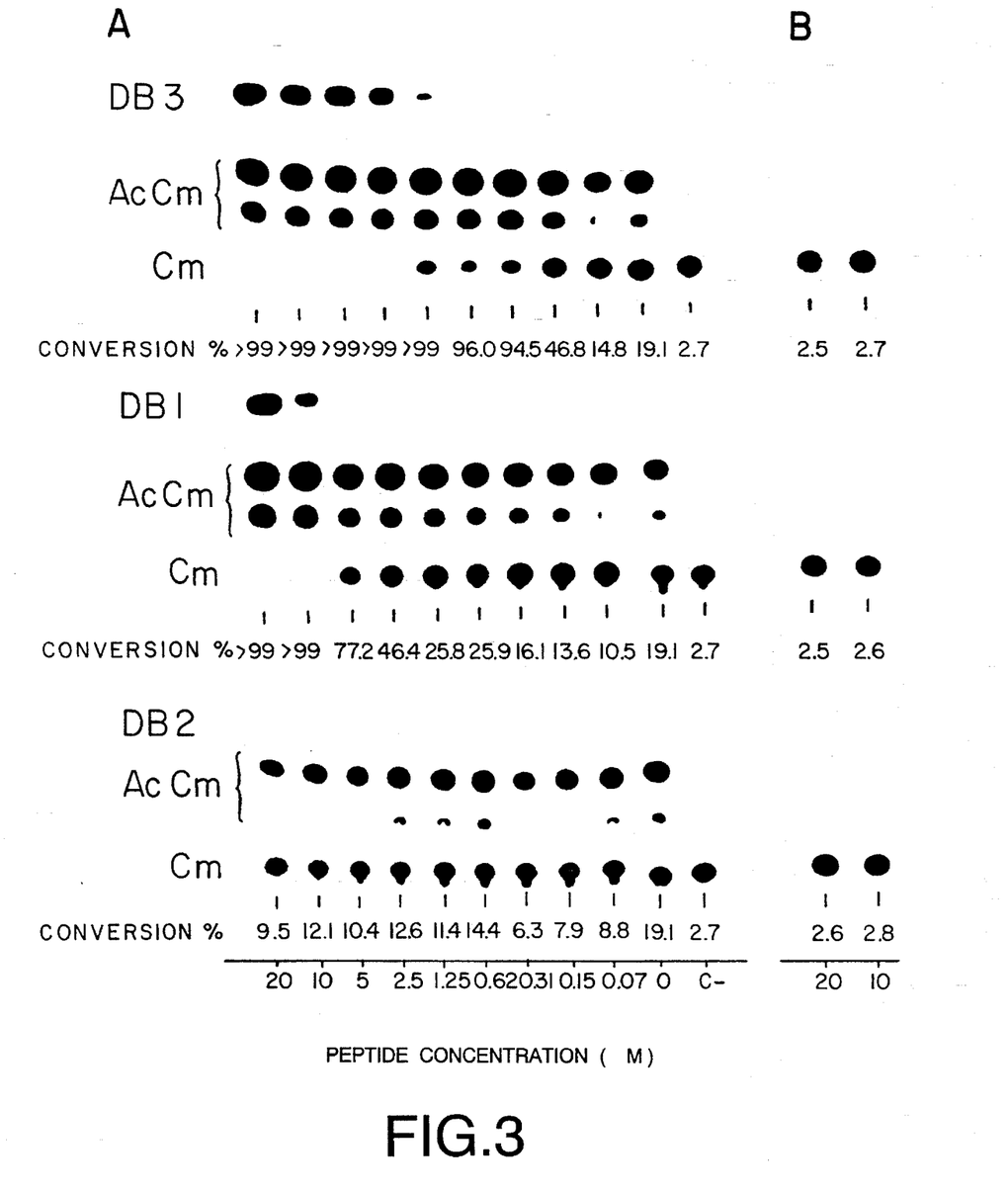
Figure 4:
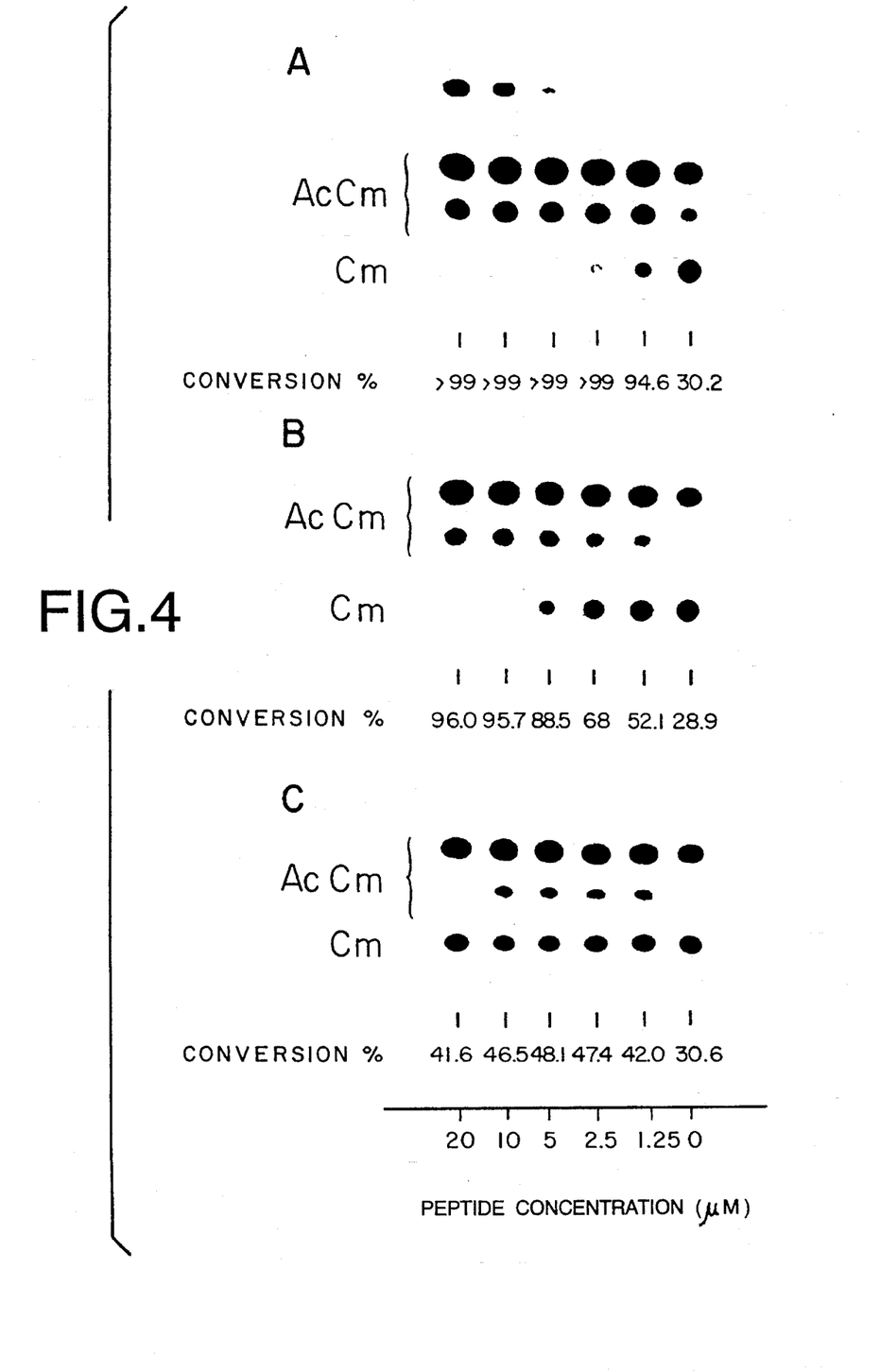
Figure 5A:
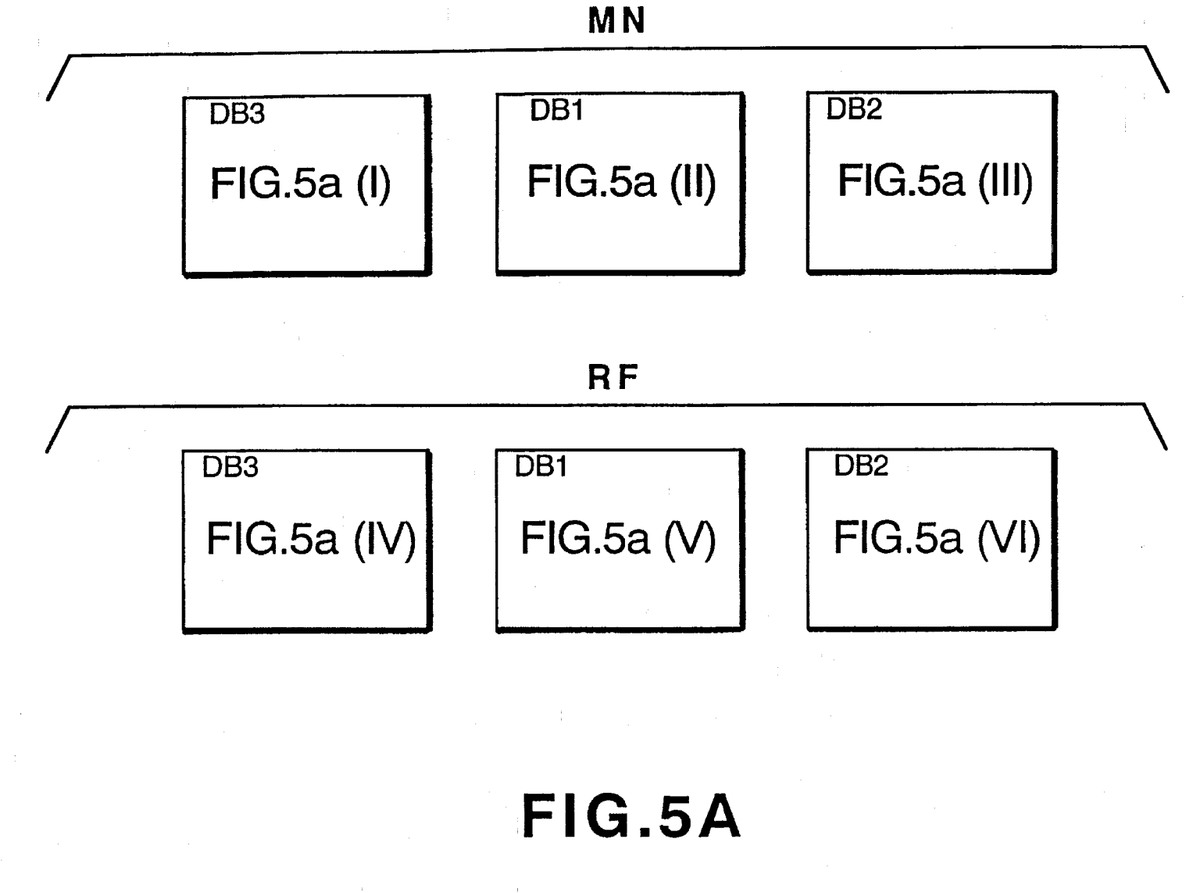
Figure 5B:
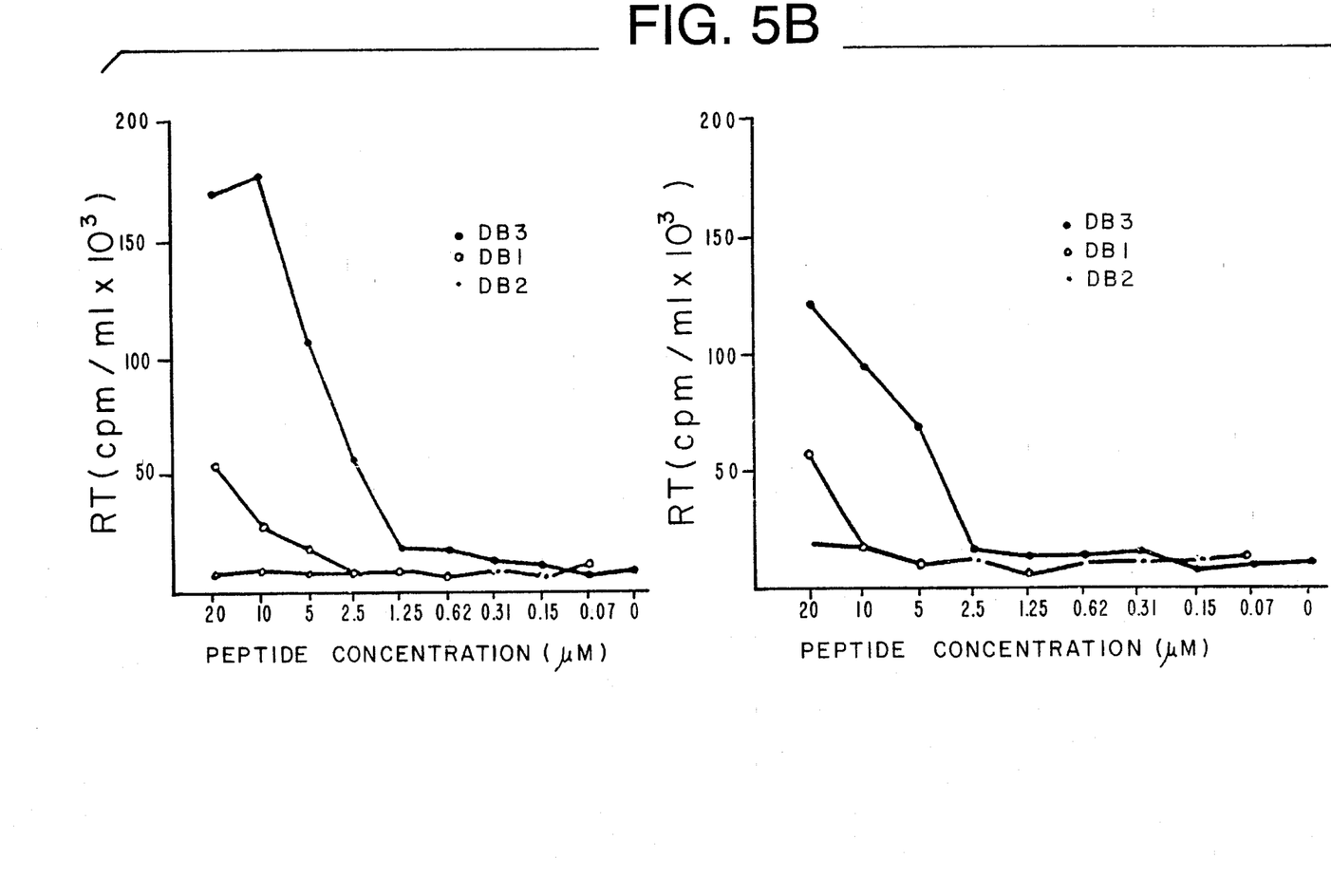
Figure 6:
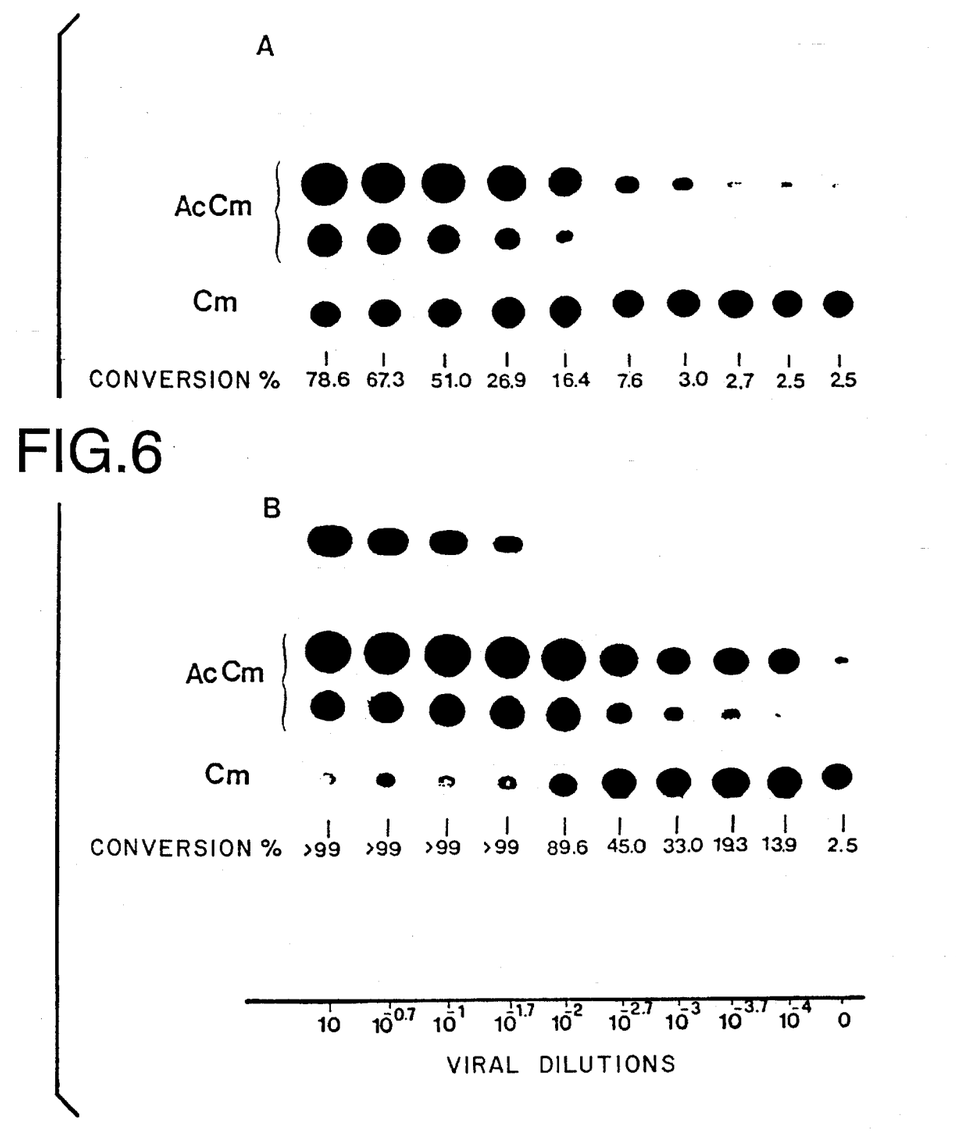
Figure 7:
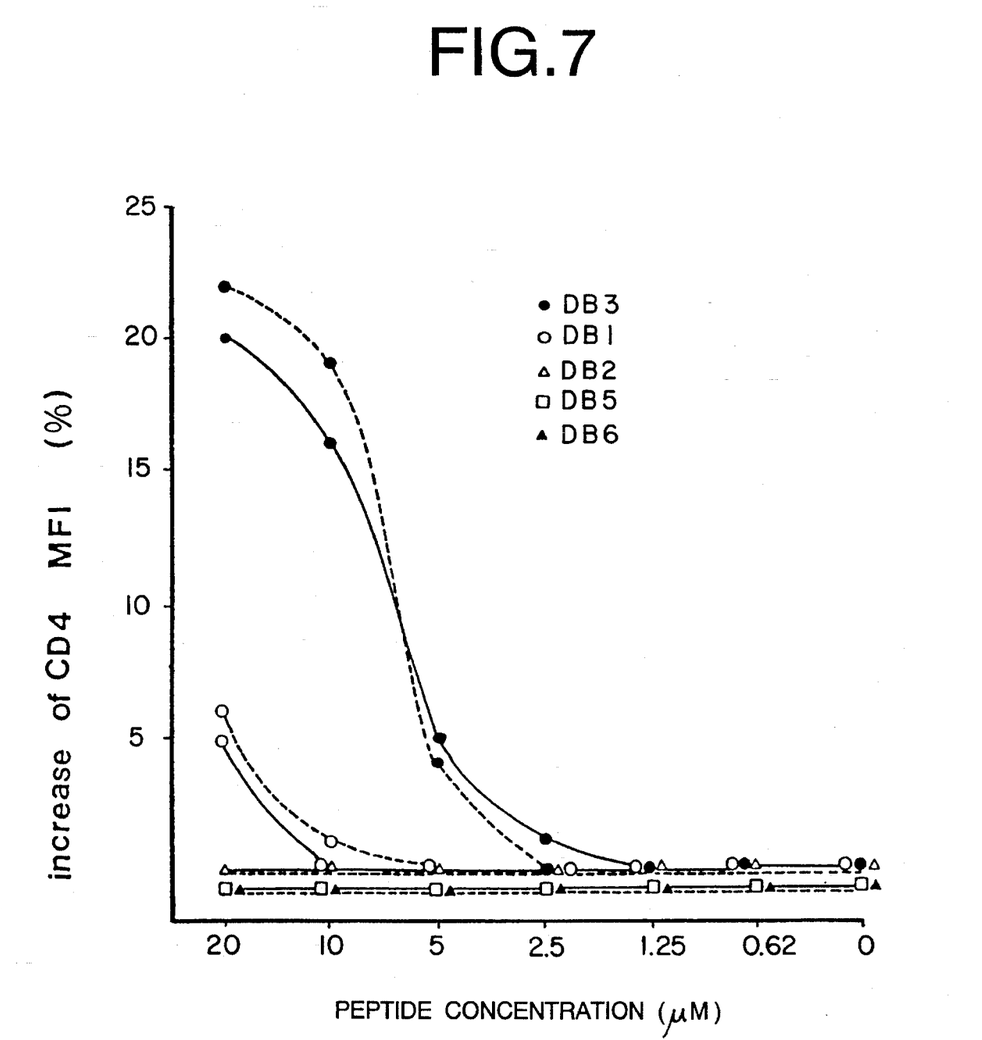

RT values (expressed in cpm/ml) in surnatants collected 4 days after infection further reflected the enhancing effect of DB3, and to a lesser extent that of DB1, on HTLV-III B strain infection, while no such increase was observed in cultures treated with peptides DB2, DB5 and DB6 also at maxima doses (FIG. 2).

These findings demonstrate that the enhanced cytopathic effect observed is the result of a more intense vital replication and of the envelope gp 120 protein expression on the surface of infected CD4 positive cells.

HIV-1 gene expression depends mainly on the sequences in the "Long Terminal Repeats" region (LTR).

LTR may be activated by vital factors as well by the transactivator (tat) protein which interacts with the responsive elements (TAR) in LTR, and cellular factors recognizing target sequences in HIV-1-LTR. (Nabel, G., and D. Baltimore. 1987. An inducible transcription factor activates expression of human immunodeficiency virus in T cell. Nature 326: 711–713) and are induced by several T-cell mitogens (Greene, W. C., E. Bohnlein, and D. Ballard. 1989. HIV-1, HTLV-I and normal T-cell growth: transcriptional strategies and surprises. Immunol. Today 10: 272–274).

The effect of the peptides on HIV-1-LTR region were evaluated using H938 cells.

These cells were permanently transfected with HIV-1-LTR bonded to CAT gene, thus LTR activation resulting in activation of CAT expression (Felber, B. K., and G. N. Pavlakis. 1988. A quantitative bioassay for HIV-1 based on trans-activation. Science 239: 184–187).

Parallel cell cultures were incubated for 1 hour with scalar dilutions of peptides, and one culture for each dilution was then infected with HTLV-III B strain.

After 48 hours both infected and non infected cells were processed for CAT assay.

As shown in FIG. 3, CAT expression, evaluated as the percentage of Cm (chloramphenicol) in AcCm (chloramphenicol in acetylated form), resulted increased in DB3 treated HIV-1 infected cultures. The effect of DB1 peptide on CAT expression is lower than that of DB3.

DB2, DB5, DB6 have no effect on CAT expression, and the value obtained are very similar to those obtained with untreated HIV-1 infected cultures.

The non infected cultures treated with peptides did not show CAT expression even at high doses.

These results demonstrate that LTR region activation is due to vital tat protein overexpression by initial enhancement of HIV-1 infection, rather than a peptide mitogenic effect on the infected cells.

Features of the Activity of the Peptides Used in the Method of the Invention A characteristic feature of the activity of the peptides used in the method of the invention is that the enhancing effect exerted by the peptides occurs in the early steps of vital infection.

To investigate this point, we treated the H938 cells with different doses of DB3 before, during and after HIV-1 infection. The enhancement effect in cells exposed for 1 hour to both virus and peptide simultaneously (FIG. 4A) was quite similar to that obtained when cells were preexposed to peptide 1 hour before infection (see FIG. 3).

Furthermore vital enhancement also occurred when cells were treated with peptide for 1 hour, washed and then infected (FIG. 4B). No enhancement was seen when cells were infected with HIV-1, and then washed to remove virtually all the virus particles still present in the medium, prior to exposure to peptide (FIG. 4C). The observation that enhancement occurred only when peptide was present in cultures before or during HIV-1 infection, but not when it was added after entry into the cells, implies that the peptides acts during the early steps of viral infection.

An other characteristic of the peptides used in the present method is that the infectivity enhancement is not virus restricted.

The antigenic properties of V3 region are known to be virus-specific; antibodies elicited by MN-derived peptide do not neutralize HTLV-III B virus and vice-versa.

Our observation that the peptide from the MN V3 neutralizing domain brought about a greater increase in HTLV-III B infection than that obtained with III B-derived specific peptide, demonstrates that the enhancement effect is not virus-restricted. To better evaluate this aspect, experiments were performed using MN and RF HIV-1 strains.

FIG. 5 shows that the peptide effect in MN and RF infection was quite similar to that observed in HTLV-III B infection (FIG. 3).

A final concentration of 20 μM DB3 increased RT values in MOLT-3 cells with MN and RF virus infected 20 and 12 times, respectively; and this effect was still evident with 0.62 μM and 5 μM in MN and RF infections, respectively (FIG. 5B).

CAT assay in H938 infected cells supported RT findings, and the increase in transactivation activity was peptide dose dependent (FIG. 5A).

As previously observed with HTLV-III B strain infection, DB1 was less effective than DB3 and brought about significant increases in both parameters only at maxima doses in both MN and RF strains infections.

Interestingly, DB2 did not have any effect on heterologous MN and homologous RF virus infections.

To determine if the enhancing effect of the peptides used in the present method depended on the vital infection dose, serial dilutions of stock virus, 10 times concentrated with respect to H9/HTLV-III B surnatants, were evaluated for infection on H938 cells in the presence and absence of peptide DB3 (10 μM final solution) by CAT assay. It was found that Cm conversion in untreated cells decreased linearly according to the vital dilution, and at $10^{-3}$ the signal was comparable to the negative control (FIG. 6A); the peptide treated cells showed almost 100% Cm conversion up to $10^{-2}$ vital dilution, and at $10^{-4}$ Cm conversion was 13.9 % (FIG. 6B).

Therefore by means of the peptides used in the present method the vital expression was amplified even if a low virus concentration was used for infecting.

The results reported above find an important practical application since the addition of said peptides to culture of indicating cells CD4-positive increases the sensitivity in determining the virus in blood and in other biological materials of subjects infected by HIV-1.

In addition said peptides can be used in all the cultures in vitro for enhancing HIV-1 infection, and therefore they find a very important use in diagnosis of uncertain case wherein the infection is limited and the methods used up to now are not enough sensitive.

Mechanism of the Enhancement of Vital Infectivity of the Peptides Used in the Present Method Without undertaking to explain the mechanism by which the above peptides enhance HIV-1 infectivity, we report herewith the experimentation results which permit to hypothesize a possible mechanism.

As already observed vital enhancement occurred in the early steps of virus entry, probably at the virus entry into the cells. Since the vital receptor on T lymphocytes is the CD4 molecule (Sattentau, Q. J., A. G. Dalgleish, R. A. Weiss, and P. C. L. Beverley 1986 epitopes of the CD4 antigen and HIV infection,Science 234: 1120), MOLT-3 cells were exposed for 1 hour to scalar doses of different peptides, and then analyzed by cytofluorimetry for CD4 expression using OKT4 and OKT4a monoclonal antibodies (MAbs).

As reported in FIG. 7, a medium intensity fluorescence increase was recorded when cells were treated with the suitable doses of DB3.

This increase was recorded within 3 minutes of DB3 treatment, and also observed in DB3 treated cells 1 hour after the peptide had been removed by washing.

In order to better investigate the peptide effect on CD4 expression, experiments were also performed using the gangliosides GM1 and phorbol ester (Chieco-Bianchi L., M. L. Calabrò, M. Panozzo, A. De Rossi, A. Amadori, L. Callegaro and A. Siccardi 1989. CD4 modulation and inhibition of HIV-1 infectivity induced by monosiaganglioside GM1 in vitro. AIDS 3: 501–507; Nakakuma H, T. Kawaguchi, Koito A., Hattori T., Kagimoto T., and Takatsuki K., 1989 Inhibition of Human immunodeficiency virus infection of human lymphocytes by gangliosides. JPN Cancer Res. 80 :702–705); Offner, H., T. Thime , and A. A. Vanderbark 1987.

Gangliosides induce selective modulation of CD4 from helper T lymphocytes. J Immunol. 139 :3295–3305; Acres, R. B., P. J. Conion, D. Y. Mochizuki and B. Ballis, 1986. Rapid phosphorylation and modulation of the T4 antigen on cloned helper T-cells induced by phorbol myristate acetate or antigen. J. Biol. Chem. 261 :16210–16214; Jaekyoon, S., C. Doyle, Z. Zang, D. Kappes, and J. L. Strominger .1990 Structural features of the cytoplasmatic region of CD4 required for internalization. EMBO J. 9:425–434).

The incubation of $5\times10^5$ MOLT-3 cells for 1 hour with 50 μg/ml of GM1 resulted in an almost complete block of CD4 expression (FIG. 8).

When GM1 exposure was carried out 1 hour after the incubation with DB3 or DB1 peptides (20 μM final concentration) or was conducted simultaneously, cells expressed CD4 levels similar to those of GM1-untreated controls; on the contrary, 20 μM of DB2 peptide did not block the CD4 down-regulation exerted by GM1 (FIG. 8).

DB3 and DB1 effects were dose dependent; 10 μM of both peptides inhibited completely CD4 down-regulation induced by GM1; at lower doses, however, DB3 peptide was more active than DB1 in blocking GM1 activity (FIG. 9).

When $5\times10^5$ MOLT-3 cells were incubated for 4 hours with 100 ng/ml of TPA, less than 10% of cells expressed CD4 on the membrane surface.

However, if TPA exposure was preceded by 1 hour treatment with DB3 peptide (20 μM), or carried out simultaneously, almost 50% cells were still CD4 positive (FIG. 8). DB3 was less effective on TPA than on GM1, and 5 μM of peptide did not inhibit TPA-induced CD4 down regulation (FIG. 9). Unlike that observed with GM1 treatment, DB1 did not block TPA activity, even at its highest dose (FIG. 8 and FIG. 9).

Said results permit to hypothesize a mechanism of peptides action involving the cellular receptor CD4.

We claim:

1. In a method for the diagnosis of HIV-1 infection in blood or other biological materials, the improvement which comprises directly determining HIV-1 by the steps of:
   (a) preparing an in vitro culture of CD-4 positive cells;
   (b) adding to the culture prepared in step (a) an effective amount of a peptide selected from the group consisting of NNTRKSIRIQRGPGRAFVTIGKIG and YNKRKRIHIGPGRAFYTTKNIIG to enhance the sensitivity of the determination of HIV-1;
   (c) adding to the mixture obtained in step (b) a sample of blood or other biological material to be determined;
   (d) incubating the mixture of step (c); and
   (e) determining if the size of the syncytia which are formed are larger than a control which is indicative of HIV-1 infection.

2. A method as claimed in claim 1, wherein said synthetic peptide has the amino acid sequence:
   NNTRKSIRIQRGPGRAFVTIGKIG.

3. A method as claimed in claim 1, wherein said synthetic peptide has the amino acid sequence:
   YNKRKRIHIGPGRAFYTTKNIIG.

* * * * *